(12) United States Patent
Grushin

(10) Patent No.: US 7,968,608 B2
(45) Date of Patent: Jun. 28, 2011

(54) PERFLUOROALKYLATED BENZOATE SURFACTANTS

(75) Inventor: Vladimir Grushin, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 343 days.

(21) Appl. No.: 12/412,408

(22) Filed: Mar. 27, 2009

(65) Prior Publication Data

US 2010/0243954 A1    Sep. 30, 2010

Related U.S. Application Data

(60) Provisional application No. 61/039,504, filed on Mar. 26, 2008.

(51) Int. Cl.
*C09K 3/00* (2006.01)
*C07C 63/08* (2006.01)

(52) U.S. Cl. .......................................... 516/72; 560/103

(58) Field of Classification Search .................. 516/72
See application file for complete search history.

(56) References Cited

U.S. PATENT DOCUMENTS 3,271,441 A * 9/1966 Brace .......................... 560/103

OTHER PUBLICATIONS

Beletskaya et al., The Heck Reaction As a Sharpening Stone of Palladium Catalysis, Chem. Rev., vol. 100 (2000), pp. 3009-3066.
Chen et al., A General Method to Fluorous Ponytail-Substituted Aromatics, Tetrahedron Letters, vol. 42 (2001), pp. 4275-4278.
Kobayashi et al., Convenient Synthesis of 3,3,3-Trifluoropropenyl Compounds From Aromatic Aldehydes by Means of the TBAF-Mediated Horner Reaction, J. Org. Chem, vol. 67 (2002), pp. 3156-3159.
Neubert et al., The Effect of Fluorinated Terminal Chains on the Mesomorphic Properties of 4,4'-Disubstituted Phenyl Benzoates, Liquid Crystals, vol. 32, No. 6 (2005), pp. 781-795.

* cited by examiner

*Primary Examiner* — Ling-Siu Choi
*Assistant Examiner* — Chun-Cheng Wang

(57) ABSTRACT

Provided are new compounds based on salts of aromatic acids containing perfluoroalkyl substituents. The compounds can be used as surfactants.

11 Claims, No Drawings

PERFLUOROALKYLATED BENZOATE SURFACTANTS

FIELD OF INVENTION

The present invention is directed to compounds based on salts of aromatic acids containing perfluoroalkyl substituents. The compounds can be used as surfactants.

BACKGROUND

Aryl compounds bearing long fluoroalkyl chains have been used as ligands, as building blocks for advanced materials or biologically active compounds for pharmaceutical or agrochemical applications. They could also be useful for a wide variety of applications where surfactant properties are desired and/or needed. However few aryl compounds have been shown to be effective in these applications.

What is needed therefore are new aryl compounds with fluoroalkyl substituents which exhibit surfactant properties.

SUMMARY

One aspect of the present invention is a compound of Formula I, II or III:

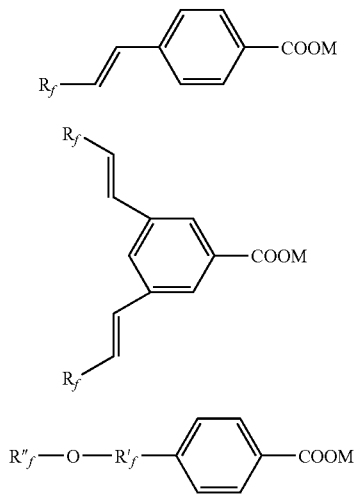

wherein M is a univalent cation, $R_f$ is independently a 1-8 carbon perfluoroalkyl group optionally substituted with ether oxygens, $R'_f$ is a perfluoroalkylene containing at least two carbons, and $R''_f$ is a perfluoroalkyl group containing at least two carbons.

Another aspect of the present invention is a surfactant comprising a compound having a Formula selected from I, II and III wherein M is $Na^+$, $K^+$, $NH_4^+$, $Li^+$, $Cs^+$, $Rb^+$, or $NR'R''R'''R''''^+$, where R', R'', R''', R'''' are independently a 1-6 carbon, linear or cyclic, alkyl or aromatic group.

A further aspect of the present invention is a method of forming an emulsion comprising: a) preparing a mixture comprising a fluorinated compound, water, and a compound having a formula selected from Formulae I to IV:

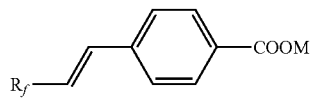

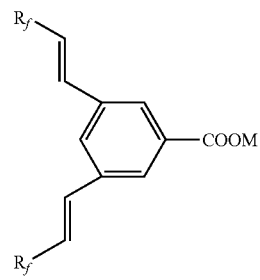

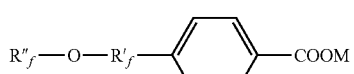

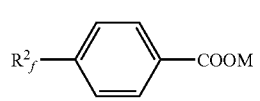

wherein M is $Na^+$, $K^+$, $NH_4^+$, $Li^+$, $Cs^+$, $Rb^+$, or $NR'R''R'''R''''^+$, where R', R'', R''', R'''' are independently a 1-6 carbon, linear or cyclic, alkyl or aromatic group, $R_f$ is independently a 1-8 carbon perfluoroalkyl group optionally substituted with ether oxygens, $R'_f$ is a perfluoroalkylene containing at least two carbons, $R''_f$ is a perfluoroalkyl group containing at least two carbons, and $R^2_f$ is independently a 1-8 carbon perfluoroalkyl group; and b) agitating the mixture until an emulsion is formed.

Another aspect of this invention is a method of altering the surface energy or interfacial free energy of a medium, said method comprising: a) providing a medium; and b) incorporating one or more compounds having a formula selected from Formulae I to IV.

DETAILED DESCRIPTION

In one embodiment, the present invention provides compounds of Formulae I, II, and III:

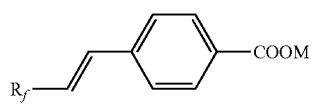

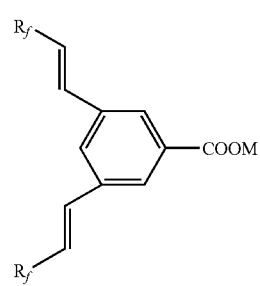

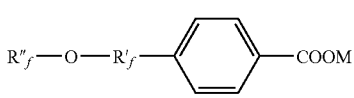

wherein M is a univalent cation, $R_f$ is independently a 1-8 carbon perfluoroalkyl group optionally substituted with ether oxygens, $R'_f$ is a perfluoroalkylene containing at least two carbons, and $R''_f$ is a perfluoroalkyl group containing at least two carbons.

By "perfluorinated alkyl" is meant a univalent group containing carbon and fluorine connected by single bonds, and optionally substituted with ether oxygens. Common examples of such perfluorinated alkyl groups include perfluorinated methyl, ethyl, propyl, isopropyl, butyl, s-butyl, isobutyl, pentyl, neopentyl, hexyl, heptyl, isoheptyl, 2-ethylhexyl, cyclohexyl and octyl, optionally substituted with one or more ether oxygens. By "perfluorinated alkylene" is meant the divalent derivative of perfluorinated alkyl, as defined above. Typically $R_f$ is independently a 4 to 6 carbon perfluoroalkyl, $C_2F_5$, $C_3F_7$, $C_4F_9$, $C_5F_{11}$, $C_6F_{13}$, $CF_2CF_2OC_2F_5$, $CF_2CF_2OC_3F_7$, or $-(CF_2)_m-X_{0-1}-CF_2-X'_{0-1}-(CF_2)_nF$ wherein X and X' are O, m is 1 to 6, and n is 1 to 6. Typically $R_f''$ is a 2 to 6 carbon perfluoroalkyl or $C_2F_5$, and $R'_f$ is a 2 to 6 carbon perfluoroalkyl or $C_2F_4$.

M can be a single cation or a mixture of one or more univalent cations, such as $H^+$, $Na^+$, $K^+$, $NH_4^+$, $Li^+$, $Cs^+$, $Rb^+$, or $NR'R''R'''R''''^+$, where R', R'', R''', R'''' are independently a 1-6 carbon, linear or cyclic, alkyl or aromatic group. Typically M is $H^+$, $Na^+$, or $K^+$.

Compounds of Formulae I to III can be prepared by any method known in the art. For Formulae I and II, one such method is the Heck coupling of aryl halides with commercially available fluoroalkyl-substituted ethylenes:

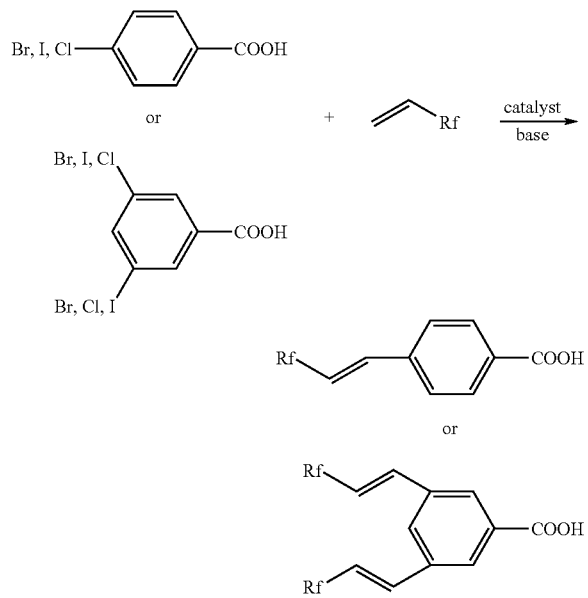

The resultant compositions can be reacted with a suitable base to produce the corresponding salts.

The Heck reaction is well known in the art and is described, for example, in *Fine Chemical Synthesis—Homogeneous*, Section 3.2. "The Heck Arylation Reaction", J. G. de Vries, Encyclopedia of Catalysis, 2002 by John Wiley & Sons, Inc., http://dx.doi.org/10.1002/0471227617.eoc090

Any standard palladium Heck catalyst can be used, typically catalysts such as $PdCl_2$, $Pd(OCOCH_3)_2$ as such or in combination with $(C_6H_5)_3P$ or $(o\text{-tolyl})_3P$, or other P containing Pd complexes such as di(μ-acetato)bis[o-(di-o-tolylphosphino)benzyl]dipalladium. The reaction is typically performed in a solvent, such as DMF or aqueous DMF, and in the presence of a base such as triethylamine, a mineral base such as potassium or sodium carbonate, $KOCOCH_3$, or $K_2HPO_4$. The reaction should be done under an inert atmosphere due to catalyst sensitivity. Reaction temperature is typically about 50° C. to 150° C. for about 24-72 hours. The di-substituted product can be achieved by adding the olefin and catalyst in quantities sufficient for exhaustive olefination of the C-halide bonds on the aromatic ring.

For compounds of Formula III, one method to prepare the compounds is via the reaction of iodo-substituted benzoic acids with at least stoichiometric amounts of copper:

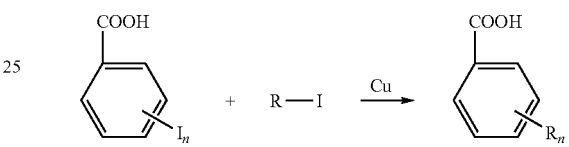

This reaction is described in Neubert et al, Liquid Crystals, Vol 32, 2005, 781-795. The resultant compounds can be reacted with a base to produce the corresponding salts. The reaction is typically performed in a solvent, such as DMSO. Reaction temperature is typically run at about 90° C. to 150° C. for about 1-6 hours.

The products may be isolated by any suitable method known in the art, such as filtration, precipitation, and/or extraction. The compounds where M is H can be converted to the salt form either before or after isolation using methods well known in the art.

Compounds described herein wherein M is not $H^+$ have been found effective in reducing the surface tension of liquids. Similarly, the compositions described herein can improve the wetting of a surface of a substrate by a liquid or coating mixture. Therefore, they are useful as surfactants in applications such as coating compositions, foams, fiber or surface protection, stabilizing dispersions, and emulsion reactions. The compositions are particularly useful in forming emulsions or dispersions with other fluorinated compounds and polymers.

By the term surfactant, or surface-active agent, is meant a substance that, when present at low concentration in a system, can adsorb onto surfaces or interfaces of the system and alter the surface or interfacial free energies of these surfaces. (Milton J. Rosen, "Surfactants and Interfacial Phenomena," Second Ed., John Wiley & 10 Sons, New York, N.Y., 1989, page 1, DOI: 10.1002/0471670561). The term interface indicates a boundary between any two immiscible phases; the term surface denotes an interface where one phase is a gas, usually air.

According to other embodiments, there is provided a method of forming an emulsion comprising: a) preparing a mixture comprising a fluorinated compound, water, and one or more compounds having a formula selected from Formulae I to IV:

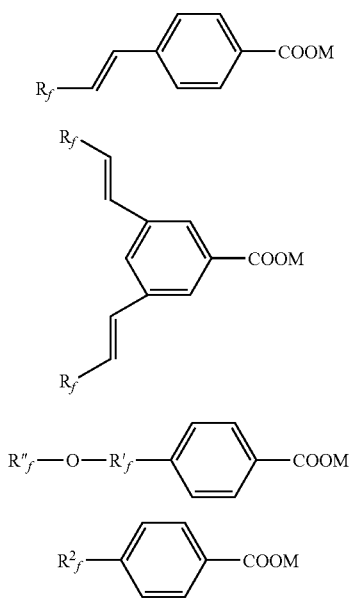

wherein M is $Na^+$, $K^+$, $NH_4^+$, $Li^+$, $Cs^+$, $Rb^+$, or $NR'R''R'''R''''^+$, where R', R'', R''', R'''' are independently a 1-6 carbon, linear or cyclic, alkyl or aromatic group, $R_f$ is independently a 1-8 carbon perfluoroalkyl group optionally substituted with ether oxygens, $R'_f$ is a perfluoroalkylene containing at least two carbons, $R''_f$ is a perfluoroalkyl group containing at least two carbons, and $R^2_f$ is independently a 1-8 carbon perfluoroalkyl group; and b) agitating the mixture until an emulsion is formed.

In other embodiments, there are provided methods for altering the surface energy of a medium, said method comprising a) providing a medium and b) incorporating one or more compounds having a formula selected from Formulae I to IV, wherein M, $R_f$, $R'_f$, $R''_f$ and $R^2_f$ are as described above, with the proviso that M is not $H^+$. The medium can be any liquid composition or mixture but is typically water or an organic liquid or mixture.

EXAMPLES

Example 1

Synthesis of P-Perfluorohexylbenzoic Acid

A mixture of perfluorohexyl iodide (11.5 g), p-iodobenzoic acid (5.0 g), copper powder (4.5 g), and DMSO (40 mL) was stirred at 100° C. for 15 min and then at 110° C. for 1.5 h. The mixture was poured into 500 mL of water. Concentrated. HCl (20 mL) was added, and the mixture was stirred for 5 min. The solids were separated by filtration, washed with water, dried, and extracted with ether. The combined blue ether extracts were evaporated to dryness and the solid residue was dissolved in a solution of KOH (11 g) in water (200 mL). The solution was filtered to separate a small quantity of dark solids. After the filtrate was acidified with conc. HCl, the precipitated white p-perfluorohexylbenzoic acid was separated by filtration, thoroughly washed with water, and dried under vacuum. The yield was 6.54 g (74%). Anal. calcd for $C_{13}H_5O_2F_{13}$, %: C, 35.5; H, 1.1. Found, %: C, 35.0; H, 1.4. $^1H$ NMR (dmso-$d_6$), δ: 7.85 (d, J=8.3 Hz, 2H, arom. H), 8.2 (d, J=8.3 Hz, 2H, arom. H), 13.5 (br s, 1H COOH). $^{19}F$ NMR (dmso-$d_6$), δ: −82.7 (t, J=9.8 Hz, 3F, $CF_3$), −112.4 (t, J=13.9 Hz, 2F, $CF_2$), −123.6 (m, 2F, $CF_2$), −123.9 (m, 2F, $CF_2$), −124.9 (m, 2F, $CF_2$), −128.1 (m, 2F, $CF_2$).

Example 2

Preparation of Potassium P-Perfluorohexylbenzoate

A mixture of p-perfluorohexylbenzoic acid (1.00 g), $KHCO_3$ (0.22 g), and water (20 mL) was stirred at heating and slowly brought almost to boil. After $CO_2$ evolution had ceased and a solid-free solution was formed the mixture was evaporated to dryness. The white residue was washed with acetone, then ether, and dried under vacuum. The yield of the potassium salt was 0.99 g (94%). Anal. Calcd for $C_{13}H_4KO_2F_{13}$, %: C, 32.6; H, 0.8. Found, %: C, 32.1; H, 0.9. $^1H$ NMR ($D_2O$), δ: 7.5 (d, J=8.3 Hz, 2H, arom. H), 7.9 (d, J=8.3 Hz, 2H, arom. H). $^{19}F$ NMR ($D_2O$), δ: −82.6 (br s, 3F, $CF_3$), −111.6 (t, J=13.6 Hz, 2F, $CF_2$), −122.6 (br m, 2F, $CF_2$), −122.8 (br m, 2F, $CF_2$), −124.0 (br m, 2F, $CF_2$), −127.5 (br m, 2F, $CF_2$).

Example 3

Preparation of Sodium P-Perfluorohexylbenzoate

A mixture of p-perfluorohexylbenzoic acid (1.00 g), $NaHCO_3$ (0.185 g), and water (20 mL) was stirred at heating and slowly brought almost to boil. After $CO_2$ evolution had ceased and a solid-free solution was formed, the mixture was evaporated to dryness. The white residue was washed with acetone, then ether, and dried under vacuum. The yield of the sodium salt was 1.01 g (99%). Anal. Calcd for $C_{13}H_4NaO_2F_{13}$, %: C, 33.8; H, 0.9. Found, %: C, 33.5; H, 1.0. $^1H$ NMR ($D_2O$), δ: 7.7 (d, J=8.0 Hz, 2H, arom. H), 8.0 (d, J=8.0 Hz, 2H, arom. H). $^{19}F$ NMR ($D_2O$), δ: −81.4 (br s, 3F, $CF_3$), −111.0 (br m, 2F, $CF_2$), −121.9 (br m, 2F, $CF_2$), −122.7 (br m, 2F, $CF_2$), −123.3 (br m, 2F, $CF_2$), −126.6 (br m, 2F, $CF_2$). The compounds prepared in Examples 2 and 3 were evaluated for surfactancy using a Kruss K11 Tensiometer at 22.1° C. Mixtures of the compounds and distilled water were prepared using a sonicator at a series of dilutions, up to 1% (weight of water/weight of compound). As can be seen in Table 1 below, the surface tension of the mixture decreased as the concentration increased.

TABLE 1

| Sample | Concentration w/w % | Surface Tension mN/m | Std. Dev. mN/m |
|---|---|---|---|
| DI Water Ex. 2 | 0 | 73.3 | 0.1 |
|  | 0.0001 | 67.8 | 0.1 |
|  | 0.001 | 48.8 | 0.1 |
|  | 0.01 | 42.6 | 0.1 |
|  | 0.1 | 27.1 | 0.1 |
|  | 1 | 19.2 | 0.1 |
| DI Water Ex. 3 | 0 | 73.3 | 0.1 |
|  | 0.0001 | 56.5 | 0.1 |
|  | 0.001 | 51.1 | 0.1 |
|  | 0.01 | 45.2 | 0.1 |
|  | 0.1 | 31.2 | 0.1 |
|  | 1 | 18.7 | 0.1 |

Example 4

Synthesis of P-Perfluorobutylbenzoic Acid

A mixture of perfluorobutyl iodide (10.6 g), p-iodobenzoic acid (5.75 g), copper powder (5.2 g), and DMSO (40 mL) was stirred in a sealed thick-wall reactor first at 70° C. for 20 min, then at 100° C. for 30 min, and finally at 110° C. for 1 h 40 min. The mixture was poured into 500 mL of water. Conc. HCl (30 mL) was added, and the mixture was stirred for 30 min. The solids were separated by filtration, washed with water, dried, and extracted with ether. The combined ether extracts were evaporated to dryness and the solid residue was stirred with a solution of KOH (15 g) in water (200 mL) for 30 min. The resulting solution was filtered to separate a small quantity of blue solids. After the filtrate was acidified with conc. HCl, the precipitated white p-perfluorobutylbenzoic acid was separated by filtration, thoroughly washed with water, and dried under vacuum. The yield was 4.4 g (56%). Anal. Calcd for $C_{11}H_5O_2F_9$, %: C, 38.8; H, 1.5. Found, %: C, 38.3; H, 1.5. $^1$H NMR (dmso-$d_6$), δ: 7.85 (d, J=8.3 Hz, 2H, arom. H), 8.2 (d, J=8.3 Hz, 2H, arom. H), 13.5 (br s, 1H COOH). $^{19}$F NMR (dmso-$d_6$), δ: −80.9 (tm, J=9.7 Hz, 3F, $CF_3$), −110.6 (tm, J=12.7 Hz, 2F, $CF_2$), −122.8 (m, 2F, $CF_2$), −125.6 (m, 2F, $CF_2$).

Example 5

Preparation of Sodium P-Perfluorobutylbenzoate

A mixture of p-perfluorobutylbenzoic acid (1.00 g), $NaHCO_3$ (0.24 g), and water (20 mL) was stirred at heating and slowly brought almost to boil. After $CO_2$ evolution had ceased and a solid-free solution was formed the mixture was evaporated to dryness. The white residue was washed with acetone, then ether, and dried under vacuum. The yield of the sodium salt was 0.97 g (94%). Anal. Calcd for $C_{11}H_4NaO_2F_9$, %: C, 36.5; H, 1.1. Found, %: C, 36.0; H, 1.1. $^1$H NMR ($D_2O$), δ: 7.75 (d, J=8.4 Hz, 2H, arom. H), 8.0 (d, J=8.4 Hz, 2H, arom. H). $^{19}$F NMR ($D_2O$), δ: −81.4 (tt, J=9.9 Hz and 3.3 Hz, 3F, $CF_3$), −111.1 (dm, J=13.0 Hz, 2F, $CF_2$), −123.4 (m, 2F, $CF_2$), −125.9 (m, 2F, $CF_2$).

Example 6

Synthesis of P-Trans-Perfluorobutylvinylidenebenzoic Acid

A mixture of p-bromobenzoic acid (8.0 g), $Na_2CO_3$ (10.0 g), and water (40 mL) was brought to boil at stirring and then cooled to room temperature. Perfluorobutylethylene (15 mL) in DMF (80 mL) and trans-di(μ-acetato)bis[o-(di-o-tolylphosphino)benzyl]dipalladium (0.38 g; prepared as described in: Herrmann et al., Chem. Eur. J. 1997, 3, 1357) were added, and the mixture was stirred sealed under $N_2$ in a thick wall reactor at 100° C. for 72 h. After cooling to room temperature the reactor was unsealed and the contents were poured into 800 mL of water. At stirring, conc. HCl (20 mL) was added, after which the precipitate was separated by filtration, washed with water, and dried under vacuum. The crude product was purified using toluene solvent and a Soxhlet extractor fitted with two nested thimbles, in which the inner thimble contained the material to be purified, and the space between the inner and outer thimble contained silica gel, as described by Halliday, Young and Grushin, Org. Lett. 2003, 5, 2003. After the extraction was complete, the toluene solution was reduced in volume and cooled in an ice bath for 2-3 h. The white crystalline solid was separated by filtration, washed with a small quantity of cold toluene, and dried under vacuum. The yield of p-trans-perfluorobutylvinylidenebenzoic acid was 7.38 g (51%). $^1$H NMR (dmso-$d_6$), δ: 6.9 (dt, J=16.2 and 12.8 Hz, 1H, $CHCF_2$), 7.45 (dt, J=16.2 and 1.9 Hz, 1H, CH—$C_6H_4$), 7.9 (d, J=8.4 Hz, 2H, arom. H), 8.0 (d, J=8.4 Hz, 2H, arom. H), 13.1 (br s, 1H COOH). $^{19}$F NMR (dmso-$d_6$), δ: −80.9 (tm, J=9.5 Hz, 3F, $CF_3$), −110.6 (m, 2F, $CF_2$), −123.9 (m, 2F, $CF_2$), −125.7 (m, 2F, $CF_2$).

Example 7

Preparation of Sodium P-Trans-Perfluorobutylvinylidenebenzoate

A mixture of p-trans-perfluorobutylvinylidenebenzoic acid (7.38 g), $NaHCO_3$ (1.62 g), and water (50 mL) was stirred at heating and slowly brought almost to boil. After $CO_2$ evolution had ceased and a solid-free solution was formed the mixture was evaporated to dryness. The white residue was washed with ether and dried under vacuum. The yield of the sodium salt was 7.41 g (99%). Anal. Calcd for $C_{13}H_6NaO_2F_9$, %: C, 40.2; H, 1.6. Found, %: C, 40.4; H, 1.9. $^1$H NMR ($D_2O$), δ: 6.3 (dt, J=16.0 and 12.3 Hz, 1H, $CHCF_2$), 7.1 (dt, J=16.0 and 2.0 Hz, 1H, CH—$C_6H_4$), 7.4 (d, J=8.3 Hz, 2H, arom. H), 7.8 (d, J=8.3 Hz, 2H, arom. H). $^{19}$F NMR ($D_2O$), δ: −82.1 (tm, J=9.6 Hz, 3F, $CF_3$), −112.0 (m, 2F, $CF_2$), −125.0 (m, 2F, $CF_2$), −126.5 (m, 2F, $CF_2$).

Example 8

Synthesis of P-3-Oxaperfluoropentylbenzoic Acid

A mixture of 3-oxaperfluoropentyl iodide (11.0 g), p-iodobenzoic acid (5.0 g), copper powder (4.5 g), and DMSO (40 mL) was vigorously stirred as the temperature was slowly raised from 25° C. to 100° C. within 1 h, and then to 110° C. Agitation was continued for 1.5 h at 110° C., after which the mixture was allowed to cool below 100° C. and poured into 500 mL of water. Concentrated. HCl (30 mL) was added, and the mixture was stirred for 5 min. The solids were separated by filtration, washed with water, dried, and extracted with ether. The combined ether extracts were evaporated to dryness and the solid residue was dissolved in a solution of KOH (10 g) in water (200 mL). The solution was filtered to separate minor insolubles a small quantity of dark solids, and the filtrate was acidified with conc. HCl. The precipitated white p-3-oxaperfluoropentylbenzoic acid was separated by filtration, thoroughly washed with water, and dried under vacuum. The yield was 1.81 g (25%). Anal. calcd for $C_{11}H_5O_3F_9$, %: C, 37.1; H, 1.4. Found, %: C, 36.9; H, 1.5. $^1$H NMR (dmso-$d_6$), δ: 7.8 (d, J=8.3 Hz, 2H, arom. H), 8.2 (d, J=8.3 Hz, 2H, arom. H), 13.5 (br s, 1H COOH). $^{19}$F NMR (dmso-$d_6$), δ: −86.6 (br s, 3F, $CF_3$), −87.1 (m, 2F, $CF_2$), −88.6 (m, 2F, $CF_2$), −114.4 (br s, 2F, $CF_2$).

Example 9

Preparation of sodium P-3-Oxaperfluoropentylbenzoate

A mixture of p-3-oxaperfluoropentylbenzoic acid (1.20 g), $NaHCO_3$ (0.28 g), and water (50 mL) was stirred at heating and slowly brought to boil. After $CO_2$ evolution had ceased and a solid-free solution was formed the mixture was evaporated to dryness. The residue was washed with acetone, then ether, and dried under vacuum. The yield of the sodium salt was 1.4 g (90%). Anal. calcd for $C_{11}H_4O_3F_9Na$, %: C, 34.9; H, 1.1. Found, %: C, 34.7; H, 1.2. $^1$H NMR ($D_2O$), δ: 7.8 (d, J=8.3 Hz, 2H, arom. H), 8.0 (d, J=8.3 Hz, 2H, arom. H) $^{19}$F NMR ($D_2O$), δ: −87.1 (br s, 3F, $CF_3$), −87.7 (m, 2F, $CF_2$), −88.9 (m, 2F, $CF_2$), −115.1 (br t, 2F, $CF_2$).

What is claimed is:

1. A compound of Formula I, II, or III:

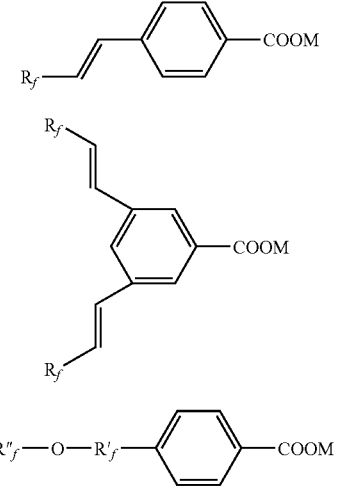

wherein M is a univalent cation, $R_f$ is independently a 1-8 carbon perfluoroalkyl group optionally substituted with ether oxygens, $R'_f$ is a perfluoroalkylene containing at least two carbons, and $R''_f$ is a perfluoroalkyl group containing at least two carbons.

2. The compound of claim 1 wherein $R_f$ is —(CF$_2$)$_m$—X$_{0-1}$—CF$_2$—X'$_{0-1}$—(CF$_2$)$_n$F wherein X and X' are O, m is 1 to 6, and n is 1 to 6.

3. The compound of claim 1 wherein $R''_f$ is $C_2F_5$ and $R'_f$ is $C_2F_4$.

4. The compound of claim 1 wherein $R_f$ is $C_4F_9$, $C_6F_{13}$, $CF_2CF_2OC_2F_5$, or $CF_2CF_2OC_3F_7$.

5. The compound of claim 1 wherein M is H$^+$, Na$^+$, K$^+$, NH$_4^+$, Li$^+$, Cs$^+$, Rb$^+$, or NR'R''R'''R''''$^+$, where R', R'', R''', R'''' are independently a linear or cyclic 1-6 carbon, alkyl or aromatic group.

6. A surfactant comprising the compound of claim 1 wherein M is Na$^+$, K$^+$, NH$_4^+$, Li$^+$, Cs$^+$, Rb$^+$, or NR'R''R'''R''''$^+$, where R', R'', R''', R'''' are independently a 1-6 carbon, linear or cyclic, alkyl or aromatic group.

7. A method of forming an emulsion comprising:
a) preparing a mixture comprising a fluorinated compound, water, and one or more compounds having a formula selected from Formulae I to IV:

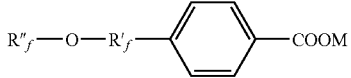

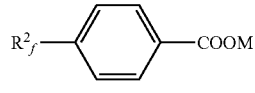

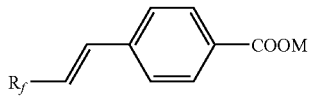

wherein M is Na$^+$, K$^+$, NH$_4^+$, Li$^+$, Cs$^+$, Rb$^+$, or NR'R''R'''R''''$^+$, where R', R'', R''', R'''' are independently a 1-6 carbon, linear or cyclic, alkyl or aromatic group, $R_f$ is independently a 1-8 carbon perfluoroalkyl group optionally substituted with ether oxygens, $R'_f$ is a perfluoroalkylene containing at least two carbons, $R''_f$ is a perfluoroalkyl group containing at least two carbons, and $R^2_f$ is independently a 1-8 carbon perfluoroalkyl group; and
b) agitating the mixture until an emulsion is formed.

8. The method of claim 7 wherein $R_f$ is —(CF$_2$)$_m$—X$_{0-1}$—CF$_2$X$_{0-1}$—(CF$_2$)$_n$F wherein X and X' are O, m is 1 to 6, and n is 1 to 6.

9. The method of claim 7 wherein $R''_f$ is $C_2F_5$ and $R'_f$ is $C_2F_4$.

10. The method of claim 7 wherein $R_f$ is $C_4F_9$, $C_6F_{13}$, $CF_2CF_2OC_2F_5$, or $CF_2CF_2OC_3F_7$.

11. A method of altering the surface energy of a medium, said method comprising:
a) providing a medium and
b) incorporating into the medium one or more compounds having a formula selected from Formulae I to IV:

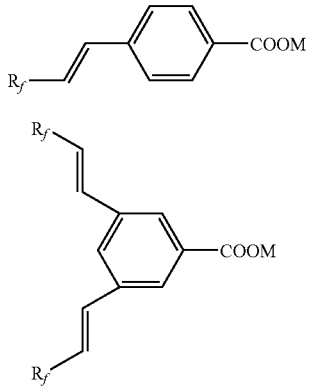

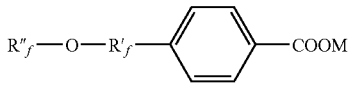

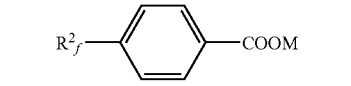

wherein M is Na$^+$, K$^+$, NH$_4^+$, Li$^+$, Cs$^+$, Rb$^+$, or NR'R''R'''R''''$^+$, where R', R'', R''', R'''' are independently a 1-6 carbon, linear or cyclic, alkyl or aromatic group, $R_f$ is independently a 1-8 carbon perfluoroalkyl group optionally substituted with ether oxygens, $R'_f$ is a perfluoroalkylene containing at least two carbons, $R''_f$ is a perfluoroalkyl group containing at least two carbons, and $R^2_f$ is independently a 1-8 carbon perfluoroalkyl group.

* * * * *